(12) United States Patent
Benz et al.

(10) Patent No.: US 11,237,116 B2
(45) Date of Patent: Feb. 1, 2022

(54) DEVICE AND METHOD FOR DETECTING CHARACTERISTICS OF A FLUID

(71) Applicant: SCAN MESSTECHNIK GESELLSCHAFT MBH, Vienna (AT)

(72) Inventors: Alexander Benz, Vienna (AT); Roman Morawek, Vienna (AT); Bernd Spigaht, Loerrach (DE); Andreas Weingartner, Korneuburg (AT)

(73) Assignee: SCAN MESSTECHNIK GESELLSCHAFT MBH, Vienna (AT)

( * ) Notice: Subject to any disclaimer, the term of this patent is extended or adjusted under 35 U.S.C. 154(b) by 54 days.

(21) Appl. No.: 16/746,718

(22) Filed: Jan. 17, 2020

(65) Prior Publication Data

US 2020/0232929 A1 Jul. 23, 2020

(30) Foreign Application Priority Data

Jan. 17, 2019 (AT) .............................. A 50037/2019

(51) Int. Cl.
*G01N 21/85* (2006.01)
*G01J 3/02* (2006.01)
*G01N 21/31* (2006.01)

(52) U.S. Cl.
CPC ........ *G01N 21/8507* (2013.01); *G01J 3/0205* (2013.01); *G01N 2021/3196* (2013.01)

(58) Field of Classification Search
CPC .. G01N 21/274; G01N 21/59; G01N 21/8507; G01N 33/1886; G01N 2021/3196; G01J 3/08; G01J 3/0205
See application file for complete search history.

(56) References Cited

U.S. PATENT DOCUMENTS

| 4,101,221 A | * | 7/1978 | Schunck | G01J 1/36 250/343 |
| 4,954,714 A | * | 9/1990 | Pollak | G01N 21/6408 250/458.1 |
| 5,357,343 A | * | 10/1994 | Lowne | G01J 3/02 356/418 |
| 5,677,534 A | * | 10/1997 | Araya | G01N 21/37 250/345 |

(Continued)

FOREIGN PATENT DOCUMENTS

| CN | 109187380 A | 1/2019 |
| DE | 10084057 B4 | 3/2012 |

(Continued)

*Primary Examiner* — Sang H Nguyen
(74) *Attorney, Agent, or Firm* — McCoy Russell LLP

(57) ABSTRACT

A device for detecting characteristics of a fluid, with a light source for emitting several light beams, of which one of the light beams is a measurement beam, which is provided for a passage through the fluid, and another light beam is a reference beam, which is provided for bypassing the fluid, with a movable cover device arranged downstream of the light source, which cover device is provided for covering the light beams and which is arranged so as to be transferable between a first position releasing the measurement beam and covering reference beam, and a second position covering the measurement beam and releasing the reference beam, and with a light detector arranged downstream of the cover device.

16 Claims, 7 Drawing Sheets

(56) References Cited

U.S. PATENT DOCUMENTS

| | | | | |
|---|---|---|---|---|
| 5,764,354 A * | 6/1998 | Aidam | ................. | G01N 21/276 |
| | | | | 250/343 |
| 6,472,657 B1 * | 10/2002 | Miles | ....................... | G01J 3/02 |
| | | | | 250/231.15 |
| 7,251,034 B2 * | 7/2007 | Kluczynski | ............ | G01N 21/39 |
| | | | | 356/437 |
| 8,035,816 B2 * | 10/2011 | Randow | ............... | G01N 21/274 |
| | | | | 356/343 |
| 8,158,945 B2 * | 4/2012 | Bitter | ................. | G01N 21/3504 |
| | | | | 250/339.13 |
| 8,779,390 B2 * | 7/2014 | Connally | ............... | G02B 21/16 |
| | | | | 250/459.1 |
| 2004/0017567 A1 * | 1/2004 | Loicht | ...................... | G01J 3/42 |
| | | | | 356/326 |
| 2013/0043391 A1 * | 2/2013 | Bitter | .................... | G01N 21/37 |
| | | | | 250/341.1 |

FOREIGN PATENT DOCUMENTS

| | | |
|---|---|---|
| GN | 103969206 A | 8/2014 |
| JP | H05332933 A | 12/1993 |

\* cited by examiner

DEVICE AND METHOD FOR DETECTING CHARACTERISTICS OF A FLUID

CROSS-REFERENCE TO RELATED APPLICATIONS

This present application claims priority to Austrian Application No. A 50037/2019 filed on Jan. 17, 2019. The entire contents of the above listed application are hereby incorporated by reference for all purposes.

TECHNICAL FIELD

The application relates to a device for detecting characteristics of a fluid which is to be examined.

In addition, the application relates to a method for detecting characteristics of a fluid which is to be examined.

BACKGROUND

Devices, in particular spectrometers, and methods for the examination of ingredients or generally of characteristics of a fluid, are known.

DE 100 84 057 B4 relates to a spectrometer for determining the ingredients of a gaseous or liquid fluid. The device comprises a light source which emits at least one measurement beam and at least one reference beam. The measurement beam is guided through a light-transmissive window into the fluid which is to be examined, and is guided back into the device again through a further light-transmissive window. In contrast, the reference beam is guided in the interior of the device past the fluid which is to be examined. Both the measurement beam and also the reference beam are received by a light detector. In order to be able to detect the light of the measurement beam and of the reference beam individually, a beam selector is provided, which respectively allows one of the light beams to pass through and interrupts the others.

By means of such devices which use a measurement beam and a reference beam, the characteristics, in particular the light transmission of a fluid which is to be examined, can be determined by a comparison of the measurement beam with the reference beam which are received with the light detector. In the case of a cloudy fluid, the measurement values of the measurement beam, received with the light detector, and of the reference beam, received with the light detector, will differ. When, on the other hand, the fluid is clear, i.e. is particularly light-transmissive, the measurement values may possibly be identical, or the difference is too small to be able to be reliably detected with low-cost measurement devices.

If, however, the measurement values for the measurement beam and the reference beam are indistinguishable, it is not comprehensible for a user of the device without suitable auxiliary equipment, i.e. only by means of the measurement values, whether the fluid is actually clear, i.e. particularly light-transmissive, or whether the beam selector, which is firstly to allow through the one and then the other of the measurement beam and of the reference beam to the light detector, is defective. A defective beam selector can therefore lead to always only the measurement beam or the reference beam being measured, although the beam selector is driven to allow the measurement beam and the reference beam to pass through alternately.

CN 103969206 A relates to a sensor for the in situ detection of a water quality, with a microprocessor, a light source, a collimated convex lens, two optical glass parts, a mechanical optical switch, a coupled convex lens, an optical detection unit and a temperature sensor, which are arranged in a closed housing.

CN 109187380 A discloses a water quality detector with a first optical path part, a sample cell, a reference cell and a second optical path part, wherein the first optical path part is used for the generating of parallel light for water sample detection. The sample cell is arranged behind the first optical path part and comprises a vessel for the placing of the contaminated water sample. The reference cell contains a reference water sample and is likewise arranged behind the first optical path part. The second optical path part is arranged behind the sample cell and the reference cell and is used for the sequential receiving and dealing with the light penetrating through the contaminated water sample and the reference water sample.

JP H05-332933 A relates to a portable measurement apparatus for detecting a concentration of $CO_2$ in respiratory air.

The three last mentioned publications also do not offer any solution for a detection of a defective beam selector.

One of the objects of the application is in the creation of a device and of a method of the type mentioned in the introduction, which allows to realize whether both the measurement beam and also the reference beam were released or allowed to pass through to the light detector. The device and the method are therefore to enable a defect of the device to be detected, which erroneously leads to always only the measurement beam or the reference beam being measured. In addition, the device is to be able to be produced in a space-saving, favourably-priced and robust manner and the method is to be able to be carried out easily and at a favourable cost.

Some of the above described problems are solved according to the application in that the cover device is arranged so as to be transferable into a third position, in which the light beams emitted from the light source are covered differently compared to the first position and the second position of the cover device, whereby an output parameter of the light detector, influenced by the light beams, in the third position is different to the output parameter of the light detector in the first position and in the second position of the cover device.

Embodiments of the device comprises a light source which is provided for emitting several light beams. The light source comprises, for this, at least one luminous element, for example at least one xenon lamp, an LED component or a laser component. Therefore, for example, the light source can comprise a single luminous element, downstream of which a beam splitter is arranged for generating several light beams. Alternatively or additionally, the light source can comprise several luminous elements which respectively generate a light beam. One of the light beams is a measurement beam which is provided for a passage through the fluid and is therefore damped depending on the ingredients (or the cloudiness) of the fluid. A fluid is understood to mean a gas, a liquid or a combination of both. The intensity of the measurement beam on exit from the fluid also depends on the intensity of the measurement beam on entry into the fluid. Therefore, another light beam is provided as reference beam, which is provided for bypassing the fluid or is not directed through the fluid. The thus undamped reference beam serves in a known manner for a comparison with the measurement beam, in order to be able to take into account or respectively compensate reductions, for example due to deterioration, of the light energy emitted by the light source when detecting the measurement beam.

In some embodiments, the measurement beam and the reference beam are emitted from the same luminous element. A movable cover device is arranged downstream of the light source, which cover device is provided for covering the light beams in different ways. For this, the cover device is arranged so as to be transferable between a first position and a second position. The cover device is configured to release (in other words expose) the measurement beam in the first position and to cover the reference beam, and in the second position to cover the measurement beam and to release (expose) the reference beam. A releasing (exposing) position is understood to mean a position of the cover device in which the light beam is at least partially allowed to pass through by the cover device, for example is substantially entirely allowed to pass through or is unimpaired.

The cover device is configured so as to be opaque or at least light-damping. Therefore, a covering position is understood to mean a position of the cover device in which the light beam is not allowed to pass through by the cover device or is only allowed to pass through in an attenuated manner. In each case, in the releasing position a greater proportion of the light beam is allowed through than in the covering position. In the first position of the cover device therefore the measurement beam can pass through the cover device substantially in an unimpeded manner, and can be detected after leaving the fluid. In order to avoid interferences to the measurement result, the reference beam is covered in this first position. In the second position of the cover device, on the other hand, the reference beam can pass through the cover device substantially unimpeded and be detected. In order to prevent interferences of the measurement result of the reference beam, the measurement beam is covered in this second position.

In order to be able to detect the measurement beam and the reference beam, a light detector is arranged downstream of the cover device, viewed starting from the light source. The light detector is configured to generate or alter an output parameter depending on the luminosity or light intensity of the incident light. For example, the output parameter is an electrical signal which the light detector provides at its output. The output parameter can, however, also be a light-dependent internal resistance of the light detector, which can be measured between connections of the light detector.

In order to be able to reliably deduce a movement or respectively switching of the cover device between the first and the second position, the cover device is arranged so as to be transferable into a third position. In the third position, the cover device is configured to cover the light beams emitted by the light source differently compared to the first position and to the second position of the cover device. The covering in the third position takes place in such a way that the output parameter of the light detector, which output parameter is influenced by the light beams, is different in the third position to the output parameter of the light detector in the first position and in the second position of the cover device. For example, in the first, second and third position, the light detector generates different electrical voltage signals at an output of the light detector or its internal resistance assumes different values. The cover device is arranged to be able to generate different light conditions at the light detector in the third position compared to the first and second position, so that a movement of the cover device can be deduced therefrom. If the light conditions were identical in the three positions, therefore a motion blockade of the cover device can be deduced, and repair measures can be undertaken.

Numerous possibilities exist as to how the cover device can cover the light beams in the third position, in order to generate different light conditions at the light detector compared to the first and second position. In addition, the various covering possibilities can depend on the light intensities of the light beams which are emitted from the light source.

When within the present description reference is made to a first position, a second position and/or a third position, this is to be understood to mean the first, second and/or third position of the cover device, in so far as nothing is indicated to the contrary.

When, furthermore, within the present description reference is made to a measurement or detection of the measurement beam or reference beam or of another light beam, this is to be understood to mean a measurement or detection of a physical quantity of the measurement beam, reference beam or other light beam, for example the light intensity, in so far as nothing is indicated to the contrary. The measurement or detection is performed by the light detector or with the help of the light detector.

In addition, within the present description, a comparison, a measurement or a difference of the output parameter(s) of the light detector refers to the value of the output parameter(s) or to measurable characteristics of the output parameter(s), in so far as nothing is indicated to the contrary. For example, voltage values available at the output of a light detector or signal forms or resistance values of the light detector are measured and compared.

According to an embodiment of the application, provision is made that in the third position of the cover device, the measurement beam or the reference beam is partially covered or an additional light beam, emitted from the light source, as second reference beam, which is provided for bypassing the fluid, in the third position of the cover device is covered differently compared to the first position and to the second position of the cover device. In this way, in the third position, compared to the first and second position, different light conditions can be generated at the light detector. When the light source only emits the measurement beam and the reference beam, the partial covering of one of these light beams leads to altered light conditions at the light detector. For example, in the third position the cover device can extend into a portion of the cross-sectional area of the measurement beam or of the reference beam. If, on the other hand, an additional light beam (second reference beam) is emitted from the light source, this additional light beam is released by the cover device in the third position, or at least partially covered, in a manner which differs from the releasing or covering in the first and second position. In some embodiments, the second reference beam in the first and second position of the cover device is released identically, or identically at least partially covered, so as not to influence the comparison between measurement beam and reference beam.

In some embodiments, the second reference beam is covered in the first position and in the second position of the cover device, and is at least partially released in the third position of the cover device. The covering of the second reference beam in the first position and second position of the cover device prevents an overlapping of the measurement beam and of the reference beam with the second reference beam, and can therefore increase the accuracy of the measurement of the measurement beam and reference beam. In the third position, the second reference beam is then released over at least a portion of its cross-section. The different covering of the second reference beam in the third position of the cover device, compared to the first and second position, therefore also comprises a release of the second reference beam in the third position.

According to a structurally simple embodiment, the cover device is arranged so as to be pivotable. For example, the cover device can be arranged so as to be pivotable about a rotation axis. Compared to a slidably arranged cover device, the pivotably arranged cover device can be moved in a space-saving manner between the first, second and third position. In addition, during the pivoting of the cover device, only a slight frictional resistance is to be overcome, whereby an undesired motion blockade of the cover device becomes more unlikely.

The movement of the cover device can take place in a precise manner when the cover device is connected with a stepping motor. In this case, the stepping motor moves the cover device. The stepping motor can therefore be part of the device for detecting characteristics of a fluid which is to be examined, and can be driven via an electrical control device.

For precise covering and release of the light beams which are emitted from the light source, provision can be made that the cover device is part of a beam selector arranged in the path of the light beams, which beam selector comprises a stationary cover plate with through-openings for the light beams, and the cover device is arranged movably for the adjustable covering of the through-openings. In embodiments, the beam selector makes provision that only selected light beams can impact on the light detector. Therefore, the cover plate of the beam selector, apart from the through-openings for the light beams, blocks the light propagation from the light source to the light detector. The through-openings of the cover plate are arranged in the propagation direction of the light beams and can be optionally released or covered with the movable cover device. The cover device can also be arranged for a partial covering of the through-openings.

For a simple construction, provision can be made that the cover device is formed by a single cover element. Thereby, it is not necessary to provide each light beam with its own cover element.

In some embodiments, the cover element may be formed by a plate, movable in a plane parallel to the plane of the stationary cover plate of the beam selector, which movable plate comprises a through-opening for one of the light beams. In this way, a light beam can be released for the passage to the light detector, by the through-opening of the movable plate being aligned in a line with one of the through-openings of the stationary cover plate of the beam selector. The through-opening of the movable plate may be configured here to allow a single light beam to pass through, while the other light beams are covered by the movable plate. One arrangement of the movable plate in a plane parallel to the plane of the stationary cover plate of the beam selector enables a space-saving construction of the entire device.

In order to assist a user in determining a motion blockade of the cover device, a processing unit can be provided downstream of the light detector, which processing unit is configured for the detection of a motion blockade of the cover device by a comparison of the output parameters of the light detector in the first position, the second position and the third position of the cover device. Through the provision of the processing unit, the user saves comparing the output parameters of the light detector himself, for instance the values of the output parameters of the light detector, in the first, second and third position of the cover device. For example, the processing unit automatically compares electrical signals generated by the light detector, which depend on the incident light intensity at the light detector. In this case, the processing unit is connected downstream of the light detector or the processing unit is connected with an output of the light detector. The processing unit can comprise a microprocessor, non-volatile memory, and instructions or suchlike. In embodiments where the light detector has no input and output, but only two connections, the processing unit is connected with these connections and is likewise regarded as being connected downstream. The processing unit can be configured to detect a motion blockade when the output parameters (or respectively the values thereof) of the light detector are identical in the first, second and third position of the cover device.

When the processing unit is configured for the output of a fault indication, the user can be informed, through the fault indication, about a detected motion blockade. The fault indication can be, for example, one of an acoustic, optical or tactile fault indication, an electrical signal, and an input into a data bank or a combination thereof.

In order to avoid or respectively reduce repetitions, in connection with the following description of the method, reference is also to be made to the preceding description of the device, in so far as this is applicable in principle. Likewise in connection with the description of the device, reference is to be made to the following description of the method.

Regarding the method, the problem is solved according to the application by driving the movable cover device for moving into a third position and detecting of the light beams, allowed to pass through by the cover device, with the light detector, in which third position the light beams emitted from the light source are covered differently compared to the first position and to the second position of the cover device, whereby an output parameter of the light detector, influenced by the light beams, in the third position is different to the output parameter of the light detector in the first position and in the second position of the cover device, and by comparing the output parameters of the light detector in the first position, the second position and the third position of the cover device for the detection of a motion blockade of the cover device. Therefore, several light beams are emitted from one light source. One of the light beams is a measurement beam, which is emitted for a passage through the fluid or the measurement beam is directed through a region provided for the fluid, which region lies for example outside the previously described device. Another light beam is a reference beam, which is emitted for bypassing the fluid or the reference beam is directed (guided) within the previously described device, past the region provided for the fluid. For a detection of the measurement beam, a movable cover device, arranged downstream of the light source, is driven, in order to move, in the case of a fault-free operation, into a first position releasing the measurement beam and covering the reference beam. For driving the cover device, a control device can be provided which is connected therewith. A light detector is arranged downstream of the cover device. In this first position of the cover device, the light beams which are allowed to pass through by the cover device in the direction of the light detector are detected with the light detector. For a detection of the reference beam, the movable cover device is driven, in order to move, in the case of a fault-free operation, into a second position covering the measurement beam and releasing the reference beam. In this second position of the cover device, the light beams which are allowed to pass through by the cover device in the direction of the light detector are detected with the light detector. It is immaterial here whether the cover device is firstly driven for movement into the first position and then into the second position or firstly for movement into the second position and then into the first position. This means that it is immaterial whether firstly the measurement beam or the reference beam is detected.

In order to be able to determine whether the cover device was actually able to carry out a movement from the first into the second position, or vice versa, or whether the cover device is blocked in its movement, the movable cover device is driven, in order to move into a third position. The first, second and third position constitute different positions of the cover device. In this third position of the cover device, the light beams which are allowed to pass through by the cover device in the direction of the light detector are detected with the light detector. The device is configured in such a way that in the case of fault-free operation in the third position light conditions exist at the light detector, which differ from the light conditions in the first and second position. For this, in the third position, the light beams emitted from the light source are covered differently by the cover device, compared to the first position and to the second position. The different covering in the third position takes place in such a way that an output parameter of the light detector, which output parameter is influenced by the light beams, is different in the third position to the output parameter of the light detector in the first position and in the second position of the cover device. The values (or the characteristics) of the output parameter of the light detector in the first position, the second position and the third position of the cover device are compared with one another in order to detect whether a motion blockade of the cover device is present. For example the values of the output parameter of the light detector are measured by a user with a measuring apparatus and compared with one another.

An embodiment of the method including partial covering of the measurement beam or of the reference beam in the third position of the cover device or different covering of an additional light beam, emitted from the light source as second reference beam, which is provided for bypassing the fluid, in the third position of the cover device compared to the first position and to the second position of the cover device. When a second reference beam is not emitted from the light source, the cover device is driven to partially cover the measurement beam or the reference beam in the third position and therefore to cover differently to the first and second position. For example, a portion of the cross-sectional area of the measurement beam or reference beam is covered in the third position. When, on the other hand, a second reference beam is emitted from the light source, the cover device is driven to cover this second reference beam in the third position of the cover device differently compared to the first position and to the second position of the cover device. In this embodiment, the second reference beam can also be only partially covered. The covering in the third position takes place in any case in such a way that the light detector in the case of fault-free operation detects different light conditions compared to the first and second position. Also by means of the second reference beam therefore different light conditions can be generated at the light detector.

Different light conditions at the light detector can be achieved for example by covering the second reference beam in the first position and in the second position of the cover device and at least partial releasing of the second reference beam in the third position of the cover device. Therefore, the cover device can be driven to cover the second reference beam in the first and second position, so as not to influence the measuring of the measurement beam and of the reference beam, and in the third position to at least partially release it. In the third position, the measurement beam and the reference beam can be covered as in the first or second position or also differently. The light conditions impinging at the light detector in the third position are different to the light conditions in the first and second position.

By comparing the output parameter of the light detector in the third position of the cover device with the output parameter of the light detector in the first position or second position of the cover device in a processing unit arranged downstream of the light detector and outputting an indication, by means of the processing unit, of a motion blockade of the cover device, when the difference between the compared output parameters is below a predetermined threshold value, a motion blockade of the cover device can be detected in an automated manner. This saves a user from a manual measuring and a manual comparison of the output parameters of the light detector. The processing unit can therefore output an indication of a motion blockade of the cover device when the difference between the values of the output parameters of the light detector in the first or second position of the cover device and the value of the output parameter in the third position of the cover device is too small or is below a predetermined threshold value. The processing unit can be configured for the input or respectively setting of the threshold value.

In some embodiments, the indication of a motion blockade of the cover device is only output when the difference between the compared output parameters is below the predetermined threshold value several times in succession. In this way, an erroneous output of an indication of a motion blockade due to brief interferences on the device, can be avoided. For example, the indication of a motion blockade is only output when the said difference is below the threshold value three times, or ten times in succession. The user can therefore be informed of the motion blockade by means of the processing unit and in addition can be prompted to initiate repair measures.

When the light beams are emitted in the form of several flashes, energy can be saved compared to a continuous emission of light. In addition, the device is hereby heated less, whereby more precise measurement results of the measurement beam and of the reference beam can be achieved. In some embodiments, the individual flashes which form a light beam are added together, in order to obtain a single measurement value for the light beam. Alternatively, the individual flashes which form a light beam can be measured individually and their measurement values can be compared with the measurement values of the flashes of another light beam. The output parameter of the light detector in the first, second and third position of the cover device can therefore comprise several values in each of the three positions or a value set.

The device and the method are applicable both for the examination of characteristics of gases and also of characteristics of liquids. However, an application for the analysis of the quality of bodies of water may provide further advantages.

BRIEF DESCRIPTION OF FIGURES

The application is explained further below with the aid of, non-restrictive example embodiments with reference to the drawings.

FIGS. 1-5 are shown approximately to scale.

DETAILED DESCRIPTION

Figure 1:
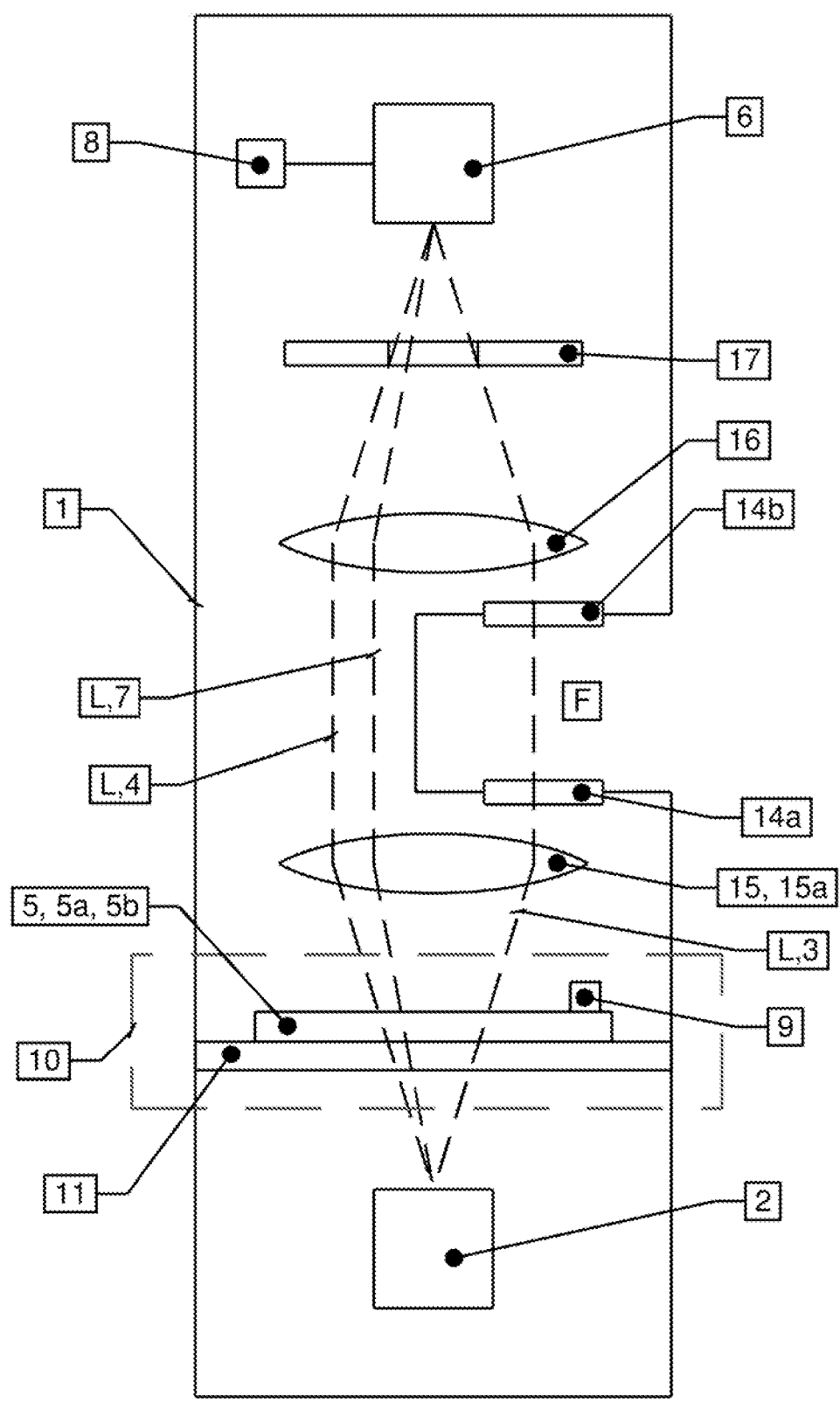
FIG. 1 depicts a schematic illustration of a device according to the application.

FIG. 1 shows a schematic illustration of an exemplary device 1 for detecting characteristics of a fluid F which is to be examined. The fluid F may be situated in a region outside the device 1. The device 1 comprises a light source 2 for the emitting of several separate light beams L. One of the light beams L is a measurement beam 3, which is provided for a passage through the fluid F. For this, the device 1 can comprise a light exit window 14a, through which the measurement beam 3 exits from the device 1, and a light entry window 14b, through which the measurement beam 3 enters into the device 1 again after passing through the fluid F. Another light beam L is a reference beam 4, which is provided for bypassing the fluid F and may be guided (in other words directed) within the device 1. The device 1 comprises, in addition, a movable or displaceable cover device 5, arranged downstream of the light source 2. The cover device 5 is therefore arranged in the path of the light beams L. The cover device 5 is provided and configured for the adjustable covering of the light beams L, for instance for covering at least one individual light beam L with simultaneous release of at least one other individual light beam L. The covering and releasing of the light beams L can also comprise a partial covering and releasing of the light beams L, when this is expedient. The cover device 5 is arranged so as to be transferable between a first position P1 releasing the measurement beam 3 and covering the reference beam 4, and a second position P2 covering the measurement beam 3 and releasing the reference beam 4 (see FIG. 2). In the example according to FIG. 1, an optical device 15, for example an optical lens 15a, for bundling the light beams L, is arranged downstream of the cover device 5. The device 1 comprises, in addition, a light detector 6, arranged downstream of the cover device 5, which light detector is provided for detecting the light beams L which are at least partially let through or released, by the cover device 5. For example, the light detector 6 can be a photoresistor, a phototransistor, a photodiode, a CMOS sensor or a CCD sensor. Between the cover device 5, for instance between the optical device 15, and the light detector 6, an optical device 16 and an aperture 17 may be are arranged for bundling or respectively directing the light beams L onto the light detector 6. The cover device 5 is, in addition, arranged so as to be transferable into a third position P3, P3', P3", in which the light beams L emitted from the light source 2 are covered differently compared to the first position P1 and to the second position P2 of the cover device 5. Hereby, an output parameter of the light detector 6, which output parameter is influenced or able to be influenced by the light beams L, comprises in the third position P3, P3', P3" a value/characteristic which is different to the value/characteristic of the output parameter of the light detector 6 in the first position P1 and in the second position P2 of the cover device 5.

In FIG. 1, furthermore, an additional light beam L, emitted from the light source 2, as second reference beam 7 is illustrated by dashed lines. The second reference beam 7 is optionally provided for bypassing the fluid F, for which it runs within the device 1.

For the movement of the cover device 5, the latter may be connected with a drive, for instance a stepping motor 9, and is driven by the latter.

In FIG. 1, furthermore, a processing unit 8 is illustrated, which is arranged downstream of the light detector 6. The processing unit 8 includes non-volatile memory storing instructions for the automatic detection of a motion blockade of the cover device 5 and if applicable, in the case of a motion blockade, for outputting a fault indication. For this, the processing unit 8 compares the values/characteristics of the output parameter of the light detector 6 in the first position P1, the second position P2 and the third position P3, P3', P3" of the cover device 5.

Figure 2:
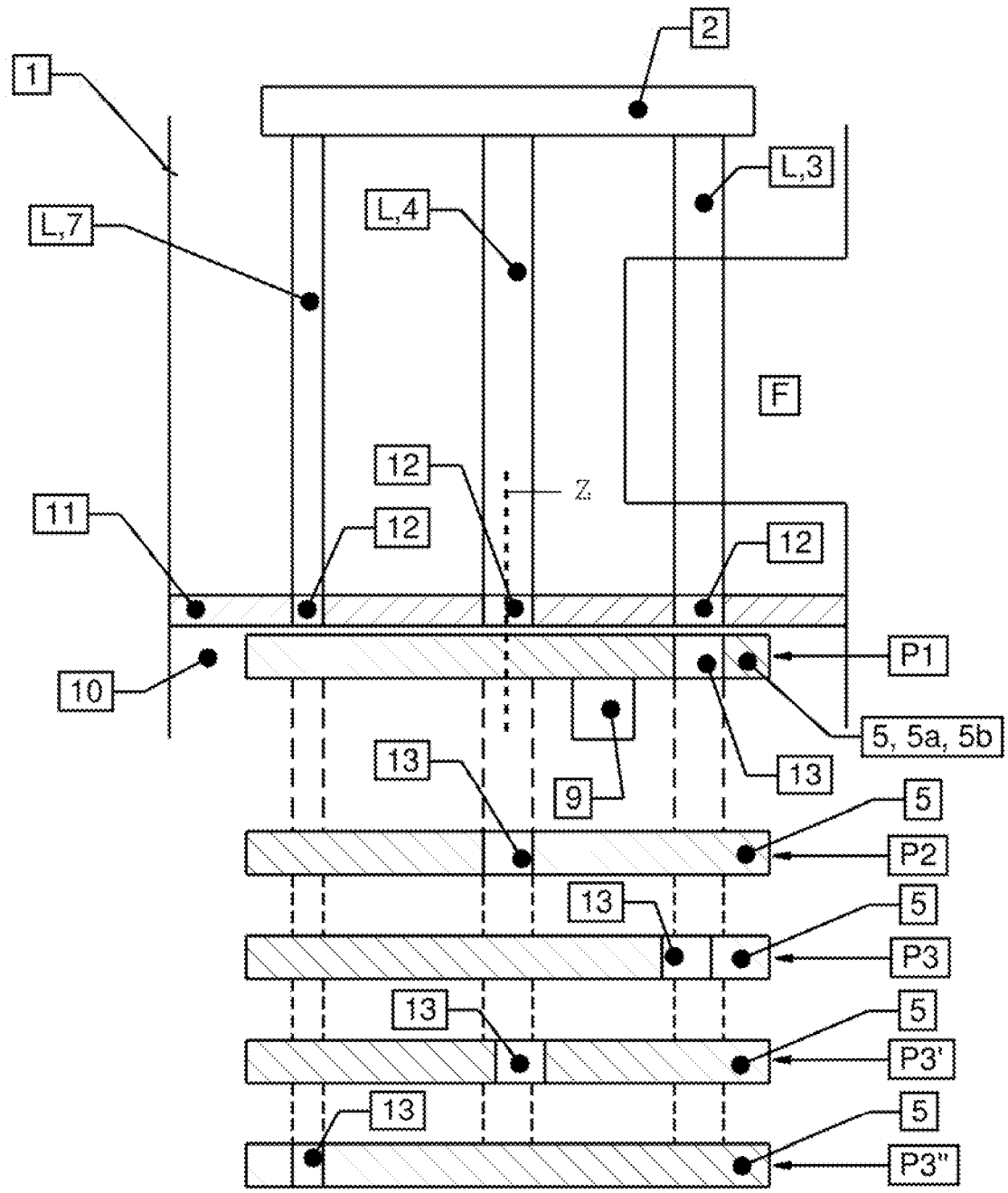
FIG. 2 depicts a schematic illustration of a measurement beam, of a reference beam and of a second reference beam and of the cover device in the first, second and third position.

FIG. 1 and FIG. 2 show schematically a light source 2, from which a measurement beam 3, a reference beam 4 and possibly a second reference beam 7 exit as light beams L. In the illustrated examples, the light beams L impinge onto a beam selector 10, which abuts at the inner circumference of the device 1, in order to avoid possible scattered light running past the beam selector 10. In the examples illustrated in FIG. 1 and FIG. 2, it can be seen that the cover device 5 is part of the beam selector 10, arranged in the path of the light beams L. Embodiments of the beam selector 10 comprise a stationary cover plate 11 with through-openings 12 (FIG. 2) for the light beams L. In order to be able to generate different light conditions to the different positions P1, P2 and P3, P3', P3" at the light detector 6, the cover device 5 is arranged so as to be movable for adjustable covering of the through-openings 12, such as for at least partial covering of the through-openings 12.

As can be seen furthermore in FIGS. 1 and 2, the cover device 5 can be formed by a single cover element 5a. The cover element 5a can be formed by a plate 5b movable in a plane parallel to the plane of the stationary cover plate 11 of the beam selector 10. The movable plate 5b comprises a through-opening 13 for the passage respectively of one of the light beams L.

FIG. 2 shows an embodiment of the cover device 5/cover element 5a/movable plate 5b in the previously mentioned first, second and third position P1, P2, P3, P3', P3". In the first position P1 of the cover device 5, the measurement beam 3 is released and the reference beam 4 is covered. In the second position P2 of the cover device 5, the measurement beam 3 is covered and the reference beam 4 is released. In the third position P3 of the cover device 5, the measurement beam 3 is partially covered and the reference beam 4 is covered. In a different third position P3' of the cover device 5, the measurement beam 3 is covered and the reference beam 4 is partially covered. In the exemplary positions P1, P2, P3 and P3' in addition the second reference beam 7 is covered. Accordingly, in the exemplary positions P1, P2, P3 and P3' the second reference beam 7 could also be omitted. In a further third position P3" of the cover device 5, the measurement beam 3 and reference beam 4 are covered and the second reference beam 7 is released. In position P3" the second reference beam 7 could also be only partially released.

Therefore, in the third position P3, P3' of the cover device 5, the measurement beam 3 or the reference beam 4 can be partially covered. Or, in the third position P3" of the cover device 5 an additional light beam L, emitted from the light source 2 as second reference beam 7, which is provided for bypassing the fluid F, can be covered differently compared to the first position P1 and to the second position P2 of the cover device 5. Here, the second reference beam 7 can be covered in the first position P1 and in the second position P2 of the cover device and can be at least partially released in the third position P3" of the cover device 5.

Figure 3:
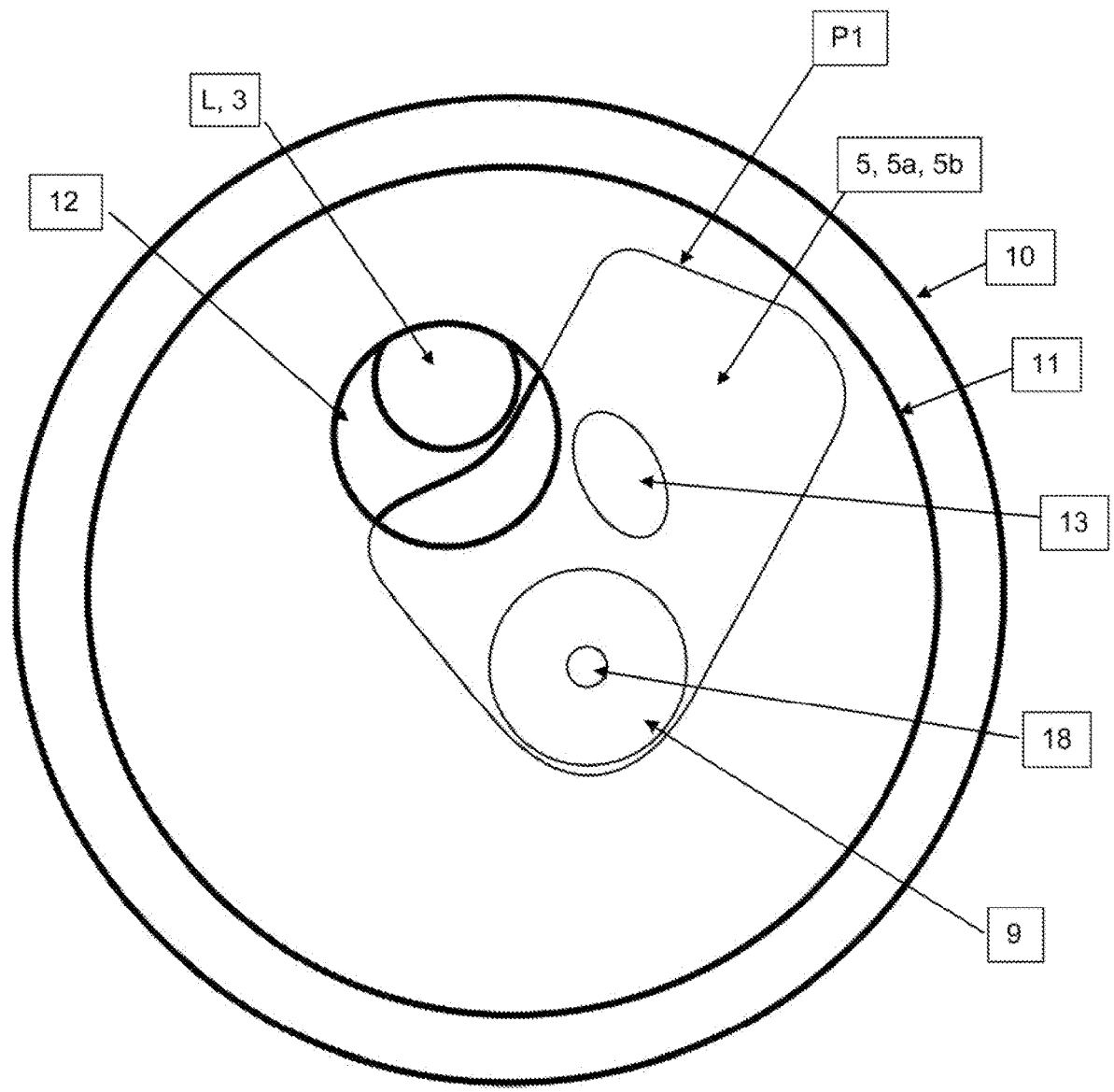
FIG. 3 depicts a detail view of an exemplary cover device in the first position.

From the description it becomes apparent that numerous combination possibilities exist for the at least partial covering and releasing of the measurement beam 3, of the reference beam 4 and of the possible second reference beam 7. In the third position P3, P3', P3" at the light detector 6 different light conditions are present than in the first position P1 and second position P2. FIG. 3 shows a detail view of an exemplary cover device 5 in the first position P1. The cover device 5 may be arranged so as to be pivotable via a pivot axis 18 in the device 1. It can also be seen in FIG. 3 that the cover device 5 can be part of a beam selector 10 arranged in the path of the light beams L, that the beam selector 10 can comprise a stationary cover plate 11 with through-openings 12 for the light beams L, and that the cover device 5 can be arranged so as to be movable for the adjustable covering of the through-openings 12. In the illustrated example, the cover device 5 is formed by a single cover element 5a, which is formed by a movable plate 5b with a through-opening 13 for respectively one of the light beams L. In the first position P1 of the cover device 5, the measurement beam 3 is released, because the cover device 5 is pivoted away from the measurement beam 3, and the reference beam 4 is covered by the cover device 5.

Figure 4:
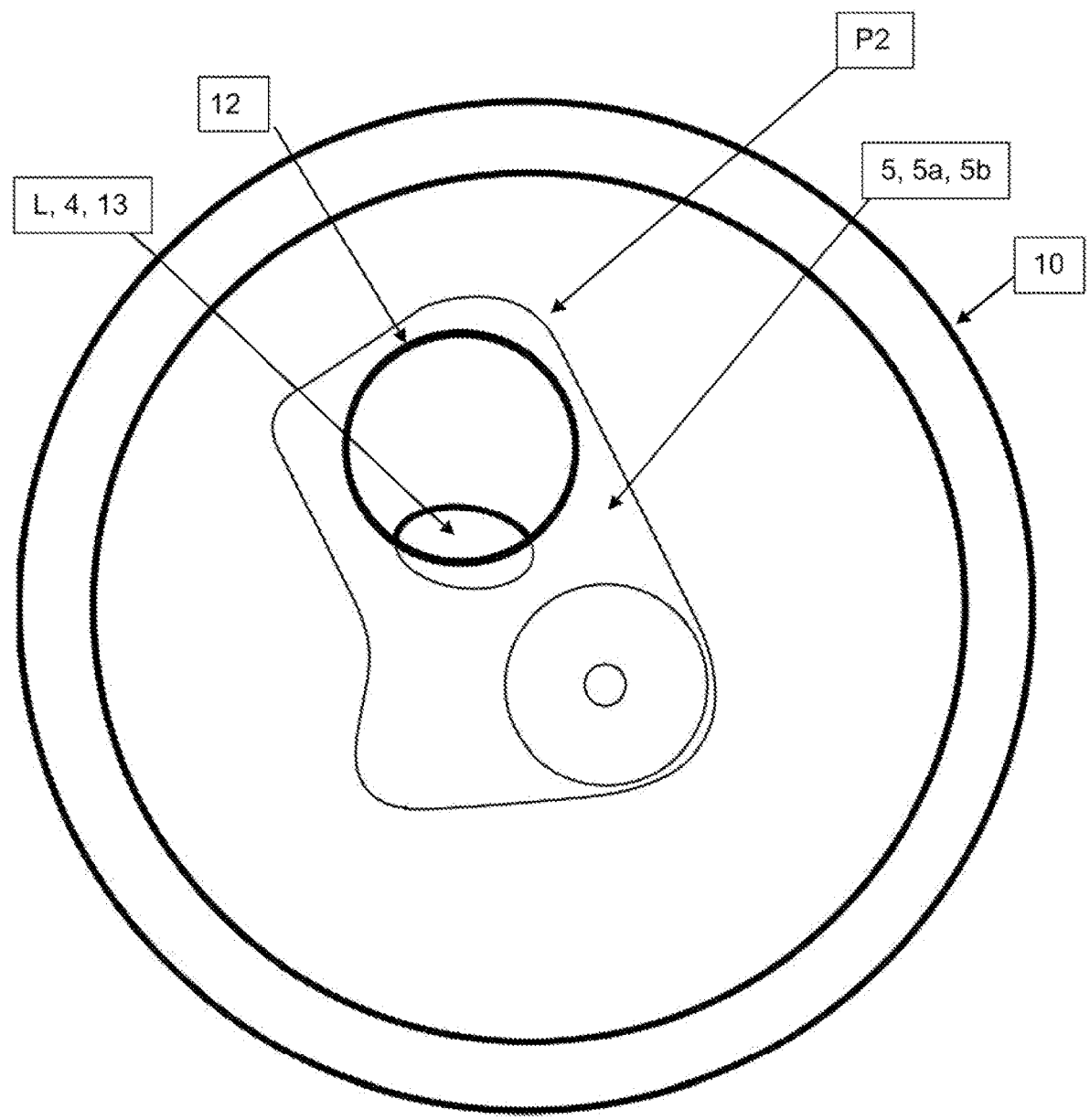
FIG. 4 depicts a detail view of the cover device of FIG. 3 in the second position.

FIG. 4 shows a detail view in which the cover device 5 was moved, for instance pivoted, into the second position P2. In this second position P2, the measurement beam 3 is covered by the cover device 5 and the reference beam 4 is released, because the through-opening 13 of the movable plate 5b and the reference beam 4 are arranged substantially in a line.

Figure 5:
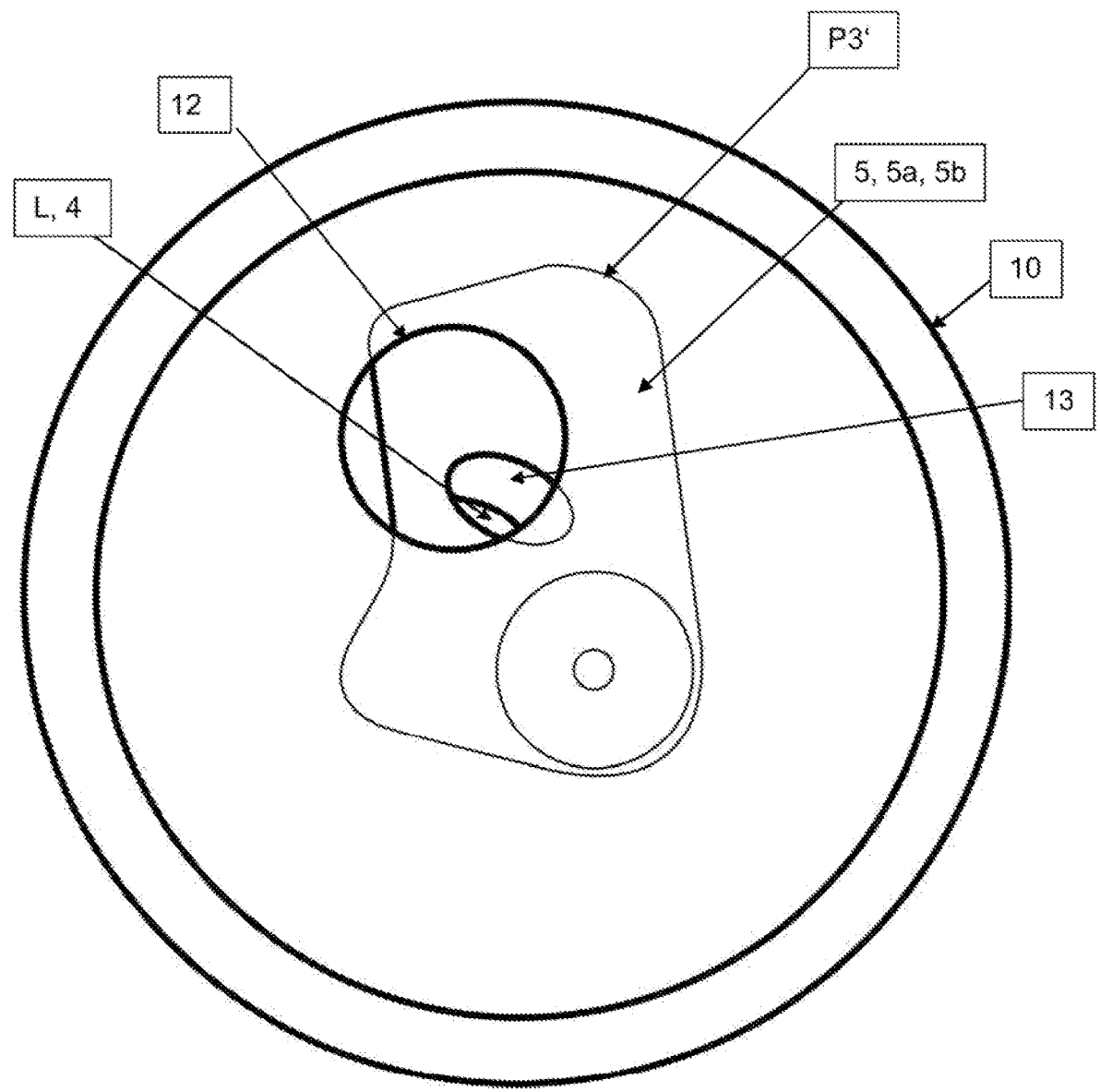
FIG. 5 depicts a detail view of the cover device of FIG. 3 in the third position.

FIG. 5 shows a further detail view in which the cover device 5 was moved, for instance pivoted, into the third position P3'. In this third position P3', the measurement beam 3 is covered by the cover device 5 and the reference beam 4 is partially released, because the through-opening 13 of the movable plate 5b and the reference beam 4 partially overlap one another.

Figure 6:
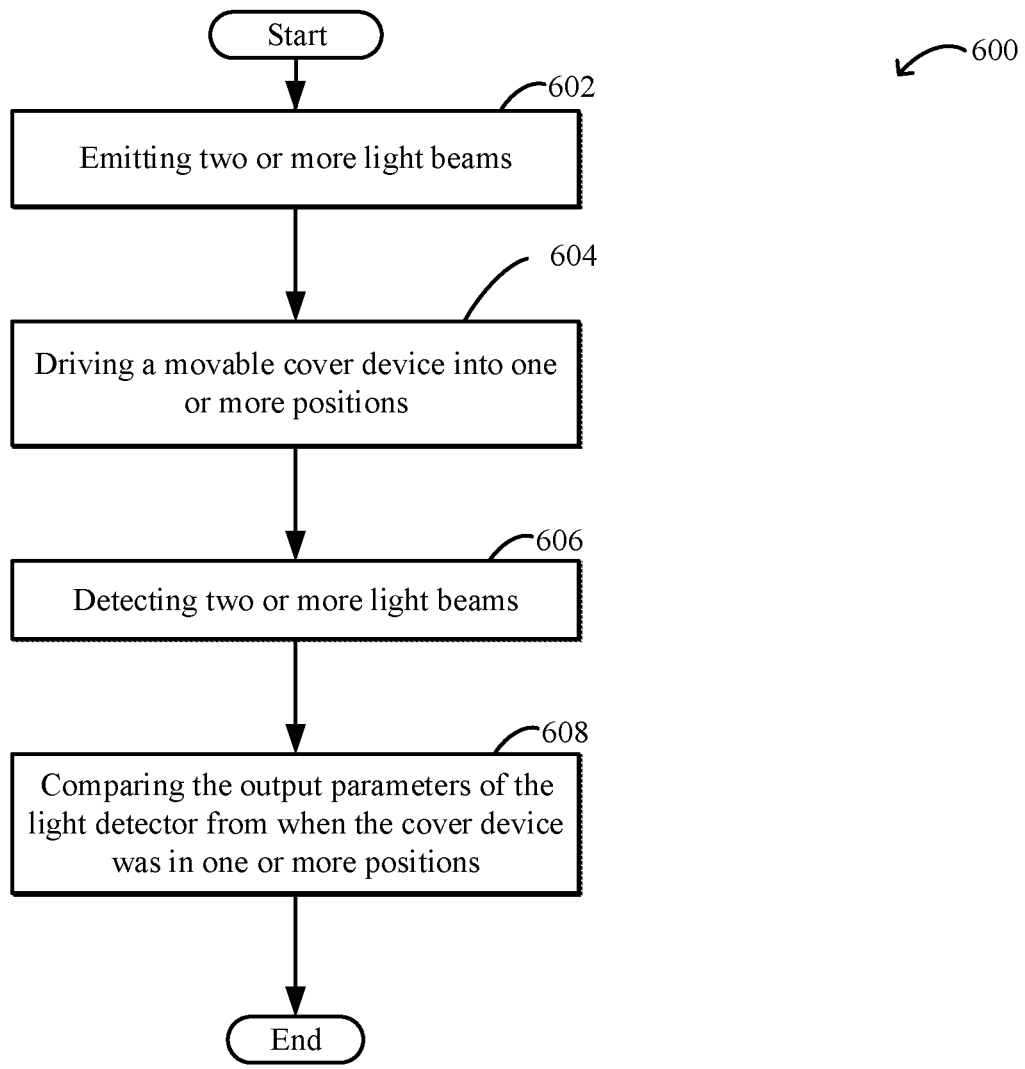
FIG. 6 depicts a method for detecting characteristics of a fluid according to the application.

FIG. 6 depicts a method 600 for detecting characteristics of a fluid comprising steps 602, 604, 606, and 608.

Figure 7:
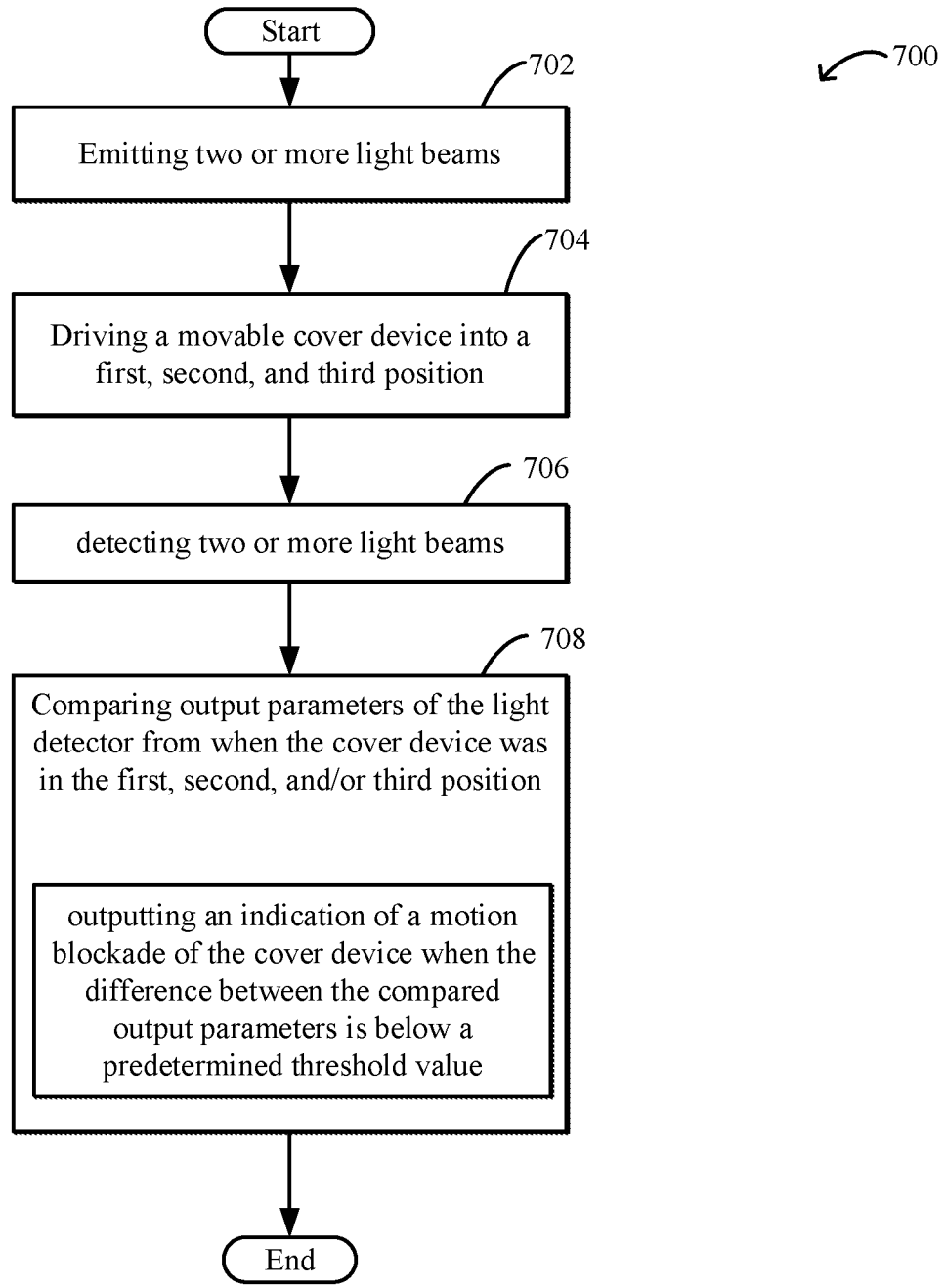
FIG. 7 depicts a further embodiment of a method according to the application.

FIG. 7 depicts a method 700 for detecting characteristics of a fluid comprising steps 702, 704, 706, and 708.

FIGS. 1-5 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

As used herein, the terms "approximately" or "substantially" are construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A device for detecting characteristics of a fluid which is to be examined, comprising:
   a light source for emitting several light beams, one of the light beams is a measurement beam, which is provided for passage through the fluid, another light beam is a reference beam, which is provided for bypassing the fluid,
   a movable cover device arranged downstream of the light source, which cover device is provided for covering the light beams and which is arranged so as to be transferable between three positions: in a first position releasing the measurement beam and covering the reference beam, in a second position covering the measurement beam and releasing the reference beam, and in a third position in which the light beams emitted from the light source are covered differently compared to the first position and to the second position of the cover device, and
   a light detector arranged downstream of the cover device, and an output parameter of the light detector, influenced by the light beams, is different when the cover device is in the third position than the output parameter of the light detector when the cover device is in the first position and in the second position, wherein a processing unit is provided, arranged downstream of the light detector, and the processing unit including non-volatile memory storing instructions for detecting a motion blockade of the cover device through a comparison of the output parameters of the light detector in the first position, the second position and the third position of the cover device.

2. The device according to claim 1, wherein in the third position of the cover device the measurement beam or, the reference beam is partially covered or an additional light beam is covered differently in the third position of the cover device compared to the first position and to the second position of the cover device, and wherein the additional light beam is emitted from the light source, as second reference beam, which is provided for bypassing the fluid.

3. The device according to claim 2, wherein the second reference beam is covered in the first position and in the second position of the cover device and is at least partially released in the third position of the cover device.

4. The device according to claim 2, wherein the cover device is formed by a single cover element.

5. The device according to claim 1, wherein the cover device is arranged so as to be pivotable.

6. The device according to claim 1, wherein the cover device is connected with a stepping motor.

7. The device according to claim 1, wherein the cover device is part of a beam selector arranged in the path of the light beams, and the beam selector comprises a stationary cover plate with through-openings for the light beams, and the cover device is arranged so as to be movable for the adjustable covering of the through-openings.

8. The device according to claim 7, wherein the cover device is formed by a single cover element.

9. The device according to claim 8, wherein the cover element is formed by a plate which is movable in a plane parallel to the plane of the stationary cover plate of the beam selector, and the movable plate comprises a through-opening for one of the light beams.

10. The device according to claim 1, further comprising instructions for outputting a fault indication.

11. A method for detecting characteristics of a fluid which is to be examined, by:

emitting several light beams from a light source, of which one of the light beams is a measurement beam, which is emitted for passage through the fluid, and another light beam is a reference beam, which is emitted for bypassing the fluid, driving a movable cover device, arranged downstream of the light source, into a first position, releasing the measurement beam and covering the reference beam, detecting the light beams, let through by the cover device, with a light detector, arranged downstream of the cover device, driving the movable cover device into a second position covering the measurement beam and releasing the reference beam, and detecting the light beams let through by the cover device with the light detector, driving the movable cover device into a third position and detecting the light beams let through by the cover device with the light detector, and in third position of the movable cover device, the light beams emitted from the light source are covered differently compared to the first position and to the second position of the movable cover device, wherein an output parameter of the light detector, influenced by the light beams, is different when the movable cover device is in the third position than the output parameter of the light detector when the movable cover device in the first position and in the second position, and comparing the output parameters of the light detector in the first position, the second position and the third position of the cover device using a processing unit arranged downstream of the light detector, for detecting a motion blockade of the cover device.

12. The method according to claim 11, wherein in the third position of the cover device, the measurement beam or, the reference beam is partially covered, or an additional light beam is covered differently in the third position of the cover device compared to the first position and to the second position of the cover device, and the additional light beam is emitted from the light source as second reference beam, which is provided for bypassing the fluid.

13. The method according to claim 12, wherein the second reference beam is covered in the first position and in the second position of the cover device and the second reference beam is at least partial released in the third position of the cover device.

14. The method according to claim 11, further comprising comparing the output parameter of the light detector in the third position of the cover device with the output parameter of the light detector in the first position or second position of the cover device using the processing unit arranged downstream of the light detector, and outputting an indication of a motion blockade of the cover device using the processing unit, when the difference between the compared output parameters is below a predetermined threshold value.

15. The method according to claim 14, wherein outputting the indication of a motion blockade of the cover device only when the difference between the compared output parameters is below the predetermined threshold value two or more times in succession.

16. The method according to claim 11, wherein emitting the light beams in the form of several flashes.

* * * * *